United States Patent [19]

Levy

[11] Patent Number: 5,085,653
[45] Date of Patent: Feb. 4, 1992

[54] DURABLE AND REUSABLE INCONTINENT UNDERPADS

[76] Inventor: Harry Levy, 219-04 Stewart Rd., Hollis Hills, N.Y. 11427

[21] Appl. No.: 625,150

[22] Filed: Dec. 10, 1990

[51] Int. Cl.⁵ .............................................. A61F 13/15
[52] U.S. Cl. .................................... 604/358; 604/365; 604/383; 604/369
[58] Field of Search ............... 604/358, 372, 378, 383, 604/385.2, 365, 366, 369

[56] References Cited

U.S. PATENT DOCUMENTS 1,353,196  9/1920  Weissman .......................... 604/358
4,943,286  7/1990  Armstead .......................... 604/358

Primary Examiner—Randall L. Green
Assistant Examiner—R. Clarke
Attorney, Agent, or Firm—Charles I. Brodsky

[57] ABSTRACT

The durable and reusable incontinent underpads of the invention are 4-layer fabrics, incorporating a first layer of woven or knit fabric, a second layer of non-woven felt, a third layer of polyurethane film, and a fourth layer of woven or knit fabric. The first and second layers are quilted together—as by stitching, or otherwise—to form a fluid absorbing portion for the underpad. The third and fourth layers are laminated together with a urethane adhesive to form a leakage preventing portion for the pad. The second and third layers are also laminated together with the urethene adhesive to complete the underpad constructions.

7 Claims, 1 Drawing Sheet

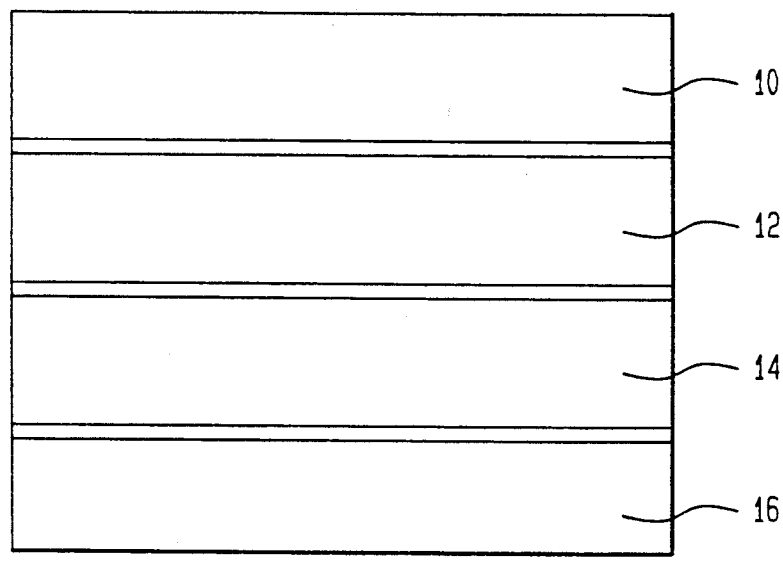

5,085,653

DURABLE AND REUSABLE INCONTINENT UNDERPADS

FIELD OF THE INVENTION

This invention relates to incontinent underpad constructions which are both durable and reusable even after hundreds of commercial washings and dryings.

BACKGROUND OF THE INVENTION

As is well known and understood, we presently live in an age where environmental issues are becoming more and more important, and the consciousness of them is increasing. One of the areas which has generated almost the greatest amount of attention in recent months has been the health-care industry, where the prod used are typically disposable in nature, and discarded by the health practitioner without a second's thought. However, as more and more of these products wash-up on the shoreline, and with the ravages of AIDS, increased attention is being given to thoughts of re-design so as to make as many of these products durable and reusable where appropriate.

One such product that is gaining a substantial degree of interest in this regard are the incontinent underpads used in hospitals, nursing facilities, old-age centers and private homes for patients who require an absorbent covering for their bedding. Such products have been introduced into the marketplace as of late, but problems have been experienced in their use as the prevalent construction employed has not proven sufficiently adequate to make those products truly durable and reusable. Analysis of the limitations has shown that a major cause of the difficulty resides in the fact that the absorbent layer—i.e., that which is closer to the individual—and the barrier layer—i.e., that which is adjacent to the bedding—are only held together on their sides, and by means of a simple sewing stitch.

While the design of such incontinent underpads is perfectly acceptable in instances where those pads are going to be disposed of, in those instances where they are to be washed—as in a commercial machine for hospitals, nursing facilities and old-age homes—and then dried for re-use, there has been found to be an uneven shrinkage between the absorbent layer and the barrier layer. This has been traced to the fact that the absorbing layer is most oftentimes composed of a non-woven felt, which tends to undergo a greater degree of shrinkage than is undergone by the materials which compose the barrier layer. As a result, the unequal size of the two layers which follow causes a substantial amount of "creasing" of the underpad, which only gets worse as additional washings follow, thus making the underpad more-and-more uncomfortable for the patient to employ.

It is an object of the invention, therefore, to modify the incontinent underpad construction so as to provide a dimensional stability to the absorbing and barrier layers which comprise the underpad, yet without affecting the absorbency ability of the pad to urine and other fluids, or the leakage preventing capability of the barrier layer.

SUMMARY OF THE INVENTION

As will become clear hereinafter, the durable and reusable incontinent underpads of the invention are 4-layer fabrics, incorporating a first layer of woven or knit fabric, a second layer of non-woven felt, a third layer of polyurethane film, and a fourth layer of woven or knit fabric. As will become clear, the first and second layers are quilted together—as by stitching, or otherwise—to form the fluid absorbing portion for the underpad. As will also become clear, the third and fourth layers are laminated together with a urethane adhesive to form the leakage-preventing portion for the pad. To complete the underpad constructions, the second and third layers will also be seen to be laminated together.

With the incontinent underpad construction embodying the invention as outlined above, the previously noted problems of "shrinkage" and "dimensional instability" were found to be eliminated and no longer existing—even after hundreds of washings and dryings in a commercial machine affording multiple wash, rinse bleach and flush cycles. In addition, the construction did not introduce any "bubbling" or evidence of "delamination" between any of the layers after these washings, and following "dryings" after each wash cycle at temperatures of 160° F.

BRIEF DESCRIPTION OF THE DRAWING

These and other features of the invention will be more clearly understood from a consideration of the sole FIGURE of the drawing showing the 4-layer fabric construction of the incontinent underpad and their manners of securement.

DETAILED DESCRIPTION OF THE DRAWING

In accordance with the invention, a 4-layer fabric is described which offers the features of laminating the absorbent portion of the underpad to its barrier portion, in a manner to provide dimensional stability to the absorbent portion without affecting the overall absorbency of the incontinent underpad or its leakage preventing characteristic. In this regard, it will be understood that the absorbent portion of the underpad is to be constructed from a woven, or knitted, fabric along with a non-woven felt, which are then quilted together. The barrier portion, on the other hand, is composed of a woven, or knitted, fabric, along with a polyurethane film which are laminated together. As will be appreciated by those skilled in the art, the absorbent layer serves to absorb any urine or fluid that might be introduced into the incontinent underpad, while the barrier layer serves to hold the urine and/or fluid internally of the pad.

Thus, in the drawing, the absorbent portion includes a first layer 10, which incorporates, as was previously mentioned, a woven, or knit, fabric which may be a 2.2 oz/yd$^2$ brushed polyester knit, a brushed nylon knit, a brushed cotton knit, a 70 denier polyester knit, any other suitable denier polyester, a nylon or cotton knit, a terry cloth, or any other blend of these materials. Such fabrics serve as the top layer of the incontinent underpad, i.e, that layer upon which the patient lies. In typical manufacture, the weight selected for the fabric employed is by-and-large determined on the basis of the particular end use to which the underpad is put. The absorbing portion of the incontinent underpad also includes a second layer 12 constructed of a non-woven felt. In carrying out the teachings of the invention, a polyester/rayon blend of fibers was found to be particularly useful, when constructed to have a thickness of 0.085 inch and a weight of 6.0 oz/yd$^2$. Although this blend proved particularly attractive in use, equally acceptable results were found to follow if a 100% polyester fiber or a 100% rayon or cotton fiber felt were used instead. In any event, the particular weight and thickness of the felt employed may again vary, depending upon the degree of absorbency needed by the particular use to which the underpad is put.

In accordance with the invention, the first layer 10 of woven, or knit, fabric is secured to the second layer 12 of non-woven felt by quilting, either with a sewing stitch process, an ultrasonic fusing process or other similar method, the type also being chosen in accordance with the types of fibers employed and upon the weights and thicknesses being employed.

The barrier portion of the incontinent underpad, on the other hand, employs yet another layer 14 of a polyurethane film, to serve as a leakage-preventing barrier to any urine, fluid, moisture, or liquids that might be present in the absorbing portion of the underpad. In a preferred construction, a polyurethane film of specific polyether urethane composition of a thickness of 0.051 mm was employed, of a nature to exhibit a water vapor permeability of 360 g/m$^2$/24 hrs., and a hydrostatic resistance of 62 psi. With a specific gravity for the polyurethane film 14 of 1.1-12 and a tensile strength of 4-10 psi, the film 14 has been noted to exhibit a very high resistance to abrasion and tearing, an elongation of over 250%, and a high chemical resistance to alkali and detergent solutions. The fourth layer of the underpad construction is shown at 16, as comprising the bottom layer—the first layer 10 comprising the top layer—, and arranged to sit adjacent to the bedding in use. As with the top layer 10, this bottom layer 16 may be of a 2.2 oz/yd$^2$ brushed polyester knit, a brushed nylon knit, a brushed cotton knit, a 70 denier polyester knit, a nylon or cotton knit, a terry cloth fabric, any other suitable denier polyester, or any blend of these fabrics. As with the top layer 10, the weight of the fabric employed in this bottom layer 16 is to be selected in accordance with the particular end use to which the incontinent underpad of the invention is to be put.

In the preferred embodiment of the invention, the two layers 14 and 16 are laminated together using a non-flammable solvent-based urethane adhesive of any manufacture. The adhesive was then applied to the polyurethane film 14 by using a cross-hatch, line-gravure, or dot-roller, and comprised a two-component polyurethane system. The laminate adhesively secured the layers 14, 16 together in this manner, and was cured using heat for reactivation, and allowed to stand for 24 hours thereafter to complete the curing process. A high water vapor permeability was produced in this manner, and gave a high level of bond strength to insure that the adhesive lamination thus resulting remained intact after machine laundering. This laminate thus formed the leakage preventing portion of the underpad.

To complete the construction of the underpad of the invention, the absorbing portion was adhesive laminated to the leakage-preventing portion in much the same manner as the layers 14 and 16 were adhesively secured. Thus, an adhesive employing a two component polyurethane system was applied between the layers 12 and 14, and a cross-hatch, line-gravure, or dot-roller method employed to secure the layers 12, 14 together. As with the lamination of the layers 14, 16, the urethane adhesive was cured using heat for reactivation, and allowed to stand for 24 hours to complete the curing process.

To test the efficacy of the 4-layer fabric construction set forth for "shrinkage" and "dimensional stability", the fabric was placed in an available washing machine of the type used in commercial operations and run through its flush, suds, rinse, bleach and sour-cycles over hundreds of times—each cycle being then followed by a "drying" at 160° before the wash cycle was repeated. In such commercial washer, an alkali solution and a detergent solution were added at the appropriate intervals, as was a sodium hypochlorate solution when bleaching was provided. In this test —where only non-ionic detergents were employed—and where no softeners were added as they tend to reduce absorbency of all fabrics, no "shrinkage" and "dimensional stability" problems were observed, even when the wash-water was soured to produce a ph of 5.5. No de-lamination was observed, nor was there any "bubbling" noted as existing between any of the layers 10-12, 12-14 or 14-16. The 4-layer fabric, after appropriate drying following 200 of these wash-cycles was observed, in each instance, to maintain size constant of each layer, and without any observable creases in the top layer 10 as would make it uncomfortable for use to a patient. At the same time, from an environmental standpoint, 4-layer fabric construction provided the incontinent underpad a high degree of durability and an equally high degree of reusability.

In the preferred embodiment of the invention, a completed construction was finalized with the lamination of the layers 12 and 14, and with the lamination of the layers 14 and 16, using an adhesive mixture formed of the composition:
1) polyurethane adhesive of viscosity 5,000 cps±2,000 cps —16.67% by weight; and
2) polyurethane adhesive of viscosity 27,000 cps±2,500 cp —83.33% by weight.

Such polyurethane adhesives are generally available and manufactured by Soluol Chemical Co., Inc., of West Warwick, R.I., under the Tradenames Solubond 1101 and Solubond 1173, respectively.

While there have been described what are considered to be preferred embodiments of the present invention, it will be readily appreciated by those skilled in the art that modifications can be made without departing from the scope of the teachings herein. For at least such reason, therefore, resort should be had to the claims appended hereto for a true understanding of the scope of the invention.

I claim:

1. A durable and reusable incontinent underpad, comprising:
   a first layer of one of woven or knit fabric;
   a second layer of non-woven felt, cooperating with said first layer providing a high absorbency characteristic for said underpad to urine, fluids, moisture and body wastes;
   a third layer of polyurethane film;
   a fourth layer of one of woven or knit fabric, cooperating with said third layer providing a high leakage preventing characteristic for said underpad to urine, fluids, moisture and body wastes absorbed by said first and second layers;
   a first adhesive lamination joining said second and third layers together;
   a second adhesive lamination joining said third and fourth layers together; and
   means quilting said first and second layers together.

2. The incontinent underpad of claim 1 wherein said means quilts said first and second layers together by stitching.

3. The incontinent underpad of claim 1 wherein said means quilts said first and second layers together by ultrasonic fusing.

4. The incontinent underpad of claim 1 wherein each of said first and second adhesive laminations incorporate a non-flammable solvent-based urethane adhesive.

5. The incontinent underpad of claim 1 wherein said first layer is composed of a brushed polyester knit of weight substantially 2.2 oz/yd$^2$.

6. The incontinent underpad of claim 1 wherein said fourth layer is composed of a brushed polyester knit of weight substantially 2.2 oz/yd$^2$.

7. The incontinent underpad of claim 1 wherein said pair of adhesive laminations include adhesive mixtures composed of the formulation by weight of:
  polyurethane adhesive of viscosity 5,000 cps±2,000 cps —16.67%; and
  polyurethane adhesive of viscosity 27,000 cps±2,500 cps —83.33%.

* * * * *